United States Patent
Mortiz et al.

(10) Patent No.: US 12,390,643 B2
(45) Date of Patent: Aug. 19, 2025

(54) HIGH FREQUENCY EPIDURAL STIMULATION TO CONTROL SENSATION

(71) Applicants: UNIVERSITY OF WASHINGTON, Seattle, WA (US); Abed Khorasani, Seattle, WA (US)

(72) Inventors: Chet T. Mortiz, Seattle, WA (US); Abed Khorasani, Seattle, WA (US); Soshi Samejima, Seattle, WA (US); Nicholas Tolley, Seattle, WA (US)

(73) Assignee: University of Washington, Seattle, WA (US)

( * ) Notice: Subject to any disclaimer, the term of this patent is extended or adjusted under 35 U.S.C. 154(b) by 382 days.

(21) Appl. No.: 18/007,948

(22) PCT Filed: Jun. 2, 2021

(86) PCT No.: PCT/US2021/035390
§ 371 (c)(1),
(2) Date: Dec. 2, 2022

(87) PCT Pub. No.: WO2021/247661
PCT Pub. Date: Dec. 9, 2021

(65) Prior Publication Data
US 2023/0271011 A1 Aug. 31, 2023

Related U.S. Application Data

(60) Provisional application No. 63/033,644, filed on Jun. 2, 2020.

(51) Int. Cl.
*A61N 1/36* (2006.01)

(52) U.S. Cl.
CPC ..... *A61N 1/36067* (2013.01); *A61N 1/36062* (2017.08); *A61N 1/36103* (2013.01);
(Continued)

(58) Field of Classification Search
CPC ............ A61N 1/36062; A61N 1/36067; A61N 1/36103; A61N 1/36139; A61N 1/36189; A61N 1/36196
See application file for complete search history.

(56) References Cited

U.S. PATENT DOCUMENTS

| 4,574,808 A | 3/1986 | Liss |
| 5,002,053 A | 3/1991 | Garcia-Rill |

(Continued)

FOREIGN PATENT DOCUMENTS

| EP | 3558448 B1 | 3/2022 |
| NL | 2013149 B1 | 4/2016 |

(Continued)

OTHER PUBLICATIONS

Robinson et al., "Canonical Correlation Analysis of EEG for Classification of Motor Imagery," 2017, IEEE International Conference on Systems, Man, and Cybernetics (SMC), pp. 2317-2321. (Year: 2017).*

(Continued)

*Primary Examiner* — George Manuel
(74) *Attorney, Agent, or Firm* — Christensen O'Connor Johnson Kindness PLLC

(57) ABSTRACT

Systems and methods for high frequency epidural stimulation to control sensation are disclosed herein. In one embodiment, a method for restoring physiological function in a subject having a neurological impairment includes generating a stimulation pattern. The stimulation pattern includes pulses at a first frequency, where the pulses of the stimulation pattern are modulated by a modulation pattern at a second frequency. The second frequency is higher than the first frequency. The method also includes stimulating a region of the spinal cord with the stimulation pattern via one or more electrodes.

18 Claims, 8 Drawing Sheets

(52) U.S. Cl.
CPC ..... *A61N 1/36139* (2013.01); *A61N 1/36189* (2013.01); *A61N 1/36196* (2013.01)

(56) References Cited

U.S. PATENT DOCUMENTS

| | | | |
|---|---|---|---|
| 9,393,409 | B2 | 7/2016 | Edgerton |
| 9,833,614 | B1 | 12/2017 | Gliner |
| 2004/0214790 | A1 | 10/2004 | Borgens |
| 2006/0253182 | A1 | 11/2006 | King |
| 2007/0178579 | A1* | 8/2007 | Ross ............... G01N 33/4836 435/283.1 |
| 2010/0211135 | A1* | 8/2010 | Caparso ............. G16H 20/70 607/62 |
| 2016/0030737 | A1 | 2/2016 | Gerasimenko |
| 2016/0121109 | A1* | 5/2016 | Edgerton ........... A61N 1/0456 607/45 |
| 2016/0166835 | A1 | 6/2016 | De Ridder |
| 2018/0093093 | A1* | 4/2018 | Courtine ............... A61B 5/24 |
| 2018/0200506 | A1 | 7/2018 | Fang |
| 2019/0083785 | A1* | 3/2019 | Tass ................. A61N 1/3605 |
| 2020/0269053 | A1* | 8/2020 | Park .................... A61B 5/37 |
| 2022/0233848 | A1* | 7/2022 | Gad ..................... A61N 1/06 |

FOREIGN PATENT DOCUMENTS

| | | |
|---|---|---|
| WO | 2016033369 A1 | 3/2016 |
| WO | 2018039117 A1 | 3/2018 |
| WO | 2019178507 A1 | 9/2019 |

OTHER PUBLICATIONS

Miller, L. E. & Herbert, W. G. Health and economic benefits of physical activity for patients with spinal cord injury. ClinicoEconomics and outcomes research: CEOR 8, 551 (2016).

WHO. International perspectives on spinal cord injury. WHO, doi:/entity/disabilities/policies/spinal_cord_injury/en/index.html (2016).

NSCISC. Spinal Cord Injury (SCI) 2016 Facts and Figures at a Glance. J Spinal Cord Med 39, 493-494, doi:10.1080/10790268. 2016.1210925 (2016).

Anderson, K. D. Targeting recovery: priorities of the spinal cord-injured population. J Neurotrauma 21, 1371-1383, doi:10.1089/neu. 2004.21.1371 (2004).

French, J. S., Anderson-Erisman, K. D. & Sutter, M. What do spinal cord injury consumers want? A review of spinal cord injury consumer priorities and neuroprosthesis from the 2008 neural interfaces conference. Neuromodulation 13, 229-231, doi:10.1111/j.1525-1403. 2009.00252.x (2010).

Lo, C., Tran, Y., Anderson, K., Craig, A. & Middleton, J. Functional priorities in persons with spinal cord injury: using discrete choice experiments to determine preferences. Journal of neurotrauma 33, 1958-1968 (2016).

Curtis, E. et al. A First-in-Human, Phase I Study of Neural Stem Cell Transplantation for Chronic Spinal Cord Injury. Cell Stem Cell 22, 941-950.e946, doi:10.1016/j.stem.2018.05.014 (2018).

Tsuji, O. et al. Concise Review: Laying the Groundwork for a First-In-Human Study of an Induced Pluripotent Stem Cell-Based Intervention for Spinal Cord Injury. Stem Cells 37, 6-13 (2019).

Panczykowski, D. M., Stone, J. G. & Okonkwo, D. O. The Management of Traumatic Spinal Cord Injury. Neurocritical Care (2018).

Badhiwala, J. H., Wilson, J. R., Kwon, B. K., Casha, S. & Fehlings, M. G. A review of clinical trials in spinal cord injury including biomarkers. Journal of neurotrauma 35, 1906-1917 (2018).

Ho, C. H. et al. Functional electrical stimulation and spinal cord injury. Physical Medicine and Rehabilitation Clinics 25, 631-654 (2014).

Enoka, R. M. & Duchateau, J. Muscle fatigue: what, why and how it influences muscle function. The Journal of physiology 586, 11-23 (2008).

Kern, H. et al. Denervated muscles in humans: limitations and problems of currently used functional electrical stimulation training protocols. Artificial organs 26, 216-218 (2002).

Mushahwar, V. K. & Horch, K. W. Selective activation and graded recruitment of functional muscle groups through spinal cord stimulation. Ann N Y Acad Sci 860, 531-535 (1998).

Bamford, J. A., Putman, C. T. & Mushahwar, V. K. Intraspinal microstimulation preferentially recruits fatigue-resistant muscle fibres and generates gradual force in rat. J Physiol 569, 873-884, doi:10. 1113/jphysiol.2005.094516 (2005).

Moritz, C. T., Lucas, T. H., Perlmutter, S. I. & Fetz, E. E. Forelimb movements and muscle responses evoked by microstimulation of cervical spinal cord in sedated monkeys. J Neurophysiol 97, 110-120, doi:10.1152/jn.00414.2006 (2007).

Zimmermann, J. B., Seki, K. & Jackson, A. Reanimating the arm and hand with intraspinal microstimulation. Journal of neural engineering 8, 054001 (2011).

Kasten, M., Sunshine, M., Secrist, E., Horner, P. J. & Moritz, C. Therapeutic intraspinal microstimulation improves forelimb function after cervical contusion injury. Journal of neural engineering 10, 044001 (2013).

Barra, B. et al. in 2018 40th Annual International Conference of the IEEE Engineering in Medicine and Biology Society (EMBC). 1424-1427 (IEEE).

Lu, D. C. et al. Engaging Cervical Spinal Cord Networks to Reenable Volitional Control of Hand Function in Tetraplegic Patients. Neurorehabil Neural Repair 30, 951-962, doi: 10.1177/ 1545968316644344 (2016).

Gad, P. et al. Non-Invasive Activation of Cervical Spinal Networks after Severe Paralysis. Journal of neurotrauma 35, 2145-2158 (2018).

Inanici, F. et al. Transcutaneous electrical spinal stimulation promotes long-term recovery of upper extremity function in chronic tetraplegia. IEEE Transactions on Neural Systems and Rehabilitation Engineering 26, 1272-1278 (2018).

Freyvert, Y. et al. Engaging cervical spinal circuitry with non-invasive spinal stimulation and buspirone to restore hand function in chronic motor complete patients. Scientific reports 8, 15546 (2018).

Wenger, N. et al. Spatiotemporal neuromodulation therapies engaging muscle synergies improve motor control after spinal cord injury. Nature medicine 22, 138 (2016).

Capogrosso, M. et al. A brain-spine interface alleviating gait deficits after spinal cord injury in primates. Nature 539, 284-288, doi: 10.1038/nature20118 (2016).

Bonizzato, M. et al. Brain-controlled modulation of spinal circuits improves recovery from spinal cord injury. Nature communications 9, 3015 (2018).

Harkema, S. et al. Effect of epidural stimulation of the lumbosacral spinal cord on voluntary movement, standing, and assisted stepping after motor complete paraplegia: a case study. Lancet 377, 1938-1947, doi:10.1016/s0140-6736(11)60547-3 (2011).

Reddy, C. G. et al. Comparison of conventional and kilohertz frequency epidural stimulation in patients undergoing trialing for spinal cord stimulation: clinical considerations. World neurosurgery 88, 586-591 (2016).

Kapural, L. et al. Novel 10-kHz High-frequency Therapy (HF10 Therapy) Is Superior to Traditional Low-frequency Spinal Cord Stimulation for the Treatment of Chronic Back and Leg PainThe SENZA-RCT Randomized Controlled Trial. Anesthesiology: The Journal of the American Society of Anesthesiologists 123, 851-860 (2015).

Deer, T. et al. Success using neuromodulation with BURST (SUN-BURST) study: results from a prospective, randomized controlled trial using a novel burst waveform. Neuromodulation: Technology at the Neural Interface 21, 56-66 (2018).

Rosenblueth, A. & Reboul, J. The blocking and deblocking effects of alternating currents on nerve. American Journal of Physiology-Legacy Content 125, 251-264 (1939).

Reboul, J. & Rosenblueth, A. The action of alternating currents upon the electrical excitability of nerve. American Journal of Physiology-Legacy Content 125, 205-215 (1939).

(56) References Cited

OTHER PUBLICATIONS

Arle, J. E., Mei, L., Carlson, K. W. & Shils, J. L. High-frequency stimulation of dorsal col. axons: potential underlying mechanism of paresthesia-free neuropathic pain relief. Neuromodulation: Technology at the Neural Interface 19, 385-397 (2016).
Bicket, M. C., Dunn, R. Y. & Ahmed, S. U. High-frequency spinal cord stimulation for chronic pain: pre-clinical overview and systematic review of controlled trials. Pain Medicine 17, 2326-2336 (2016).
Jackson, A. & Zimmermann, J. B. Neural interfaces for the brain and spinal cord-restoring motor function. Nat Rev Neurol 8, 690-699, doi: 10.1038/nmeurol.2012.219 (2012).
Moritz, C. T. Now is the critical time for engineered neuroplasticity. Neurotherapeutics, 1-7 (2018).
Collinger, J. L., Gaunt, R. A. & Schwartz, A. B. Progress towards restoring upper limb movement and sensation through intracortical brain-computer interfaces. Current Opinion in Biomedical Engineering (2018).
Aflalo, T. et al. Neurophysiology. Decoding motor imagery from the posterior parietal cortex of a tetraplegic human. Science 348, 906-910, doi:10.1126/science.aaa5417 (2015).
Collinger, J. L et al. High-performance neuroprosthetic control by an individual with tetraplegia. The Lancet 381, 557-564 (2013).
Hochberg, L. R. et al. Reach and grasp by people with tetraplegia using a neurally controlled robotic arm. Nature 485, 372 (2012).
Moritz, C. T., Perlmutter, S. I. & Fetz, E. E. Direct control of paralysed muscles by cortical neurons. Nature 456, 639 (2008).
Ethier, C., Oby, E. R., Bauman, M. J. & Miller, L. E. Restoration of grasp following paralysis through brain-controlled stimulation of muscles. Nature 485, 368 (2012).
Bouton, C. E. et al. Restoring cortical control of functional movement in a human with quadriplegia. Nature 533, 247-250, doi: 10.1038/nature17435 (2016).
Ajiboye, A. B. et al. Restoration of reaching and grasping movements through brain-controlled muscle stimulation in a person with tetraplegia: a proof-of-concept demonstration. Lancet 389, 1821-1830, doi: 10.1016/s0140-6736(17)30601-3 (2017).
Nishimura, Y., Perlmutter, S. I. & Fetz, E. E. Restoration of upper limb movement via artificial corticospinal and musculospinal connections in a monkey with spinal cord injury. Front Neural Circuits 7, 57, doi: 10.3389/ incir.2013.00057 (2013).
Zimmermann, J. B. & Jackson, A. Closed-loop control of spinal cord stimulation to restore hand function after paralysis. Front Neurosci 8, 87, doi:10.3389/fnins.2014.00087 (2014).
Moritz, C. T. et al. New perspectives on neuroengineering and neurotechnologies: NSF-DFG workshop report. IEEE Transactions on Biomedical Engineering 63, 1354-1367 (2016).
Barrese, J. C. et al. Failure mode analysis of silicon-based intracortical microelectrode arrays in non-human primates. Journal of neural engineering 10, 066014 (2013).
Simeral, J., Kim, S.-P., Black, M., Donoghue, J. & Hochberg, L. Neural control of cursor trajectory and click by a human with tetraplegia 1000 days after implant of an intracortical microelectrode array. Journal of neural engineering 8, 025027 (2011).
Campbell, A. & Wu, C. Chronically Implanted Intracranial Electrodes: Tissue Reaction and Electrical Changes. Micromachines 9, 430 (2018).
International Preliminary Report on Patentability mailed Dec. 15, 2022, issued in corresponding international Application No. PCT/US2021/035390, filed Jun. 2, 2021, 6 pages.
Hall, T. M., Nazarpour, K. & Jackson, A. Real-time estimation and biofeedback of single-neuron firing rates using local field potentials. Nature communications 5, 5462 (2014).
Russo, A. A. et al. Motor cortex embeds muscle-like commands in an untangled population response. Neuron 97, 953-966. e958 (2018).
Jackson, A. & Hall, T. M. Decoding local field potentials for neural interfaces. IEEE Transactions on Neural Systems and Rehabilitation Engineering 25, 1705-1714 (2017).
Meyer, S., Karttunen, A. H., Thijs, V., Feys, H. & Verheyden, G. How do somatosensory deficits in the arm and hand relate to upper limb impairment, activity, and participation problems after stroke? A systematic review. Physical therapy 94, 1220-1231 (2014).
Capogrosso, M. et al. A computational model for epidural electrical stimulation of spinal sensorimotor circuits. Journal of Neuroscience 33, 19326-19340 (2013).
Moraud, E. M. et al. Mechanisms underlying the neuromodulation of spinal circuits for correcting gait and balance deficits after spinal cord injury. Neuron 89, 814-828 (2016).
Formento, E. et al. Electrical spinal cord stimulation must preserve proprioception to enable locomotion in humans with spinal cord injury. Nature neuroscience 21, 1728 (2018).
Levins. A. and C.T. Moritz, "Therapeutic Stimulation for Restoration of Function After Spinal Cord Injury," Physiology 32: 391-398, 2017; Aug. 16, 2017.
Gill, Megan L. et al., "Neuromodulation of lumbosacral spinal networks enables independent stepping after complete paraplegia," Nature Medicine; vol. 24, Nov. 2018, pp. 1677-1682.
Wagner, F.B., et al., "Target neurotechnology restores walking in humans with spinal cord injury," Article; Springer Nature Limited; vol. 563, Nov. 1, 2018, pp. 65-93.
Houser, K., "Electrical Stimulation Can Effectively Restore Movement in Paralyzed Limbs," Neoscope, Futurism, Sep. 27, 2017 <https://futurism.com/neoscope/electrical-stimulation-can-effectively-restore-movement-in-paralyzed-limbs>.
Angeli, C.A., et al., "Recovery of Over-Ground Walking After Chronic Motor Complete Spinal Cord Injury," The New England Journal of Medicine, 2018; 379:1244-50.
BCC Research, "Neurostimulation: Technologies and Global Markets", Published Mar. 2014 <https://www.bccresearch.com/market-research/pharmaceuticals/neurostimulation-markets-phm149a.html>.
Paxinos, G. & Watson, C. The rat brain in stereotaxic coordinates: hard cover edition. (Elsevier, 2006).
Bansal, A. K., Truccolo, W., Vargas-Irwin, C. E. & Donoghue, J. P. Decoding 3D reach and grasp from hybrid signals in motor and premotor cortices: spikes, multiunit activity, and local field potentials. J Neurophysiol 107, 1337-1355, doi:10.1152/jn.00781.2011 (2012).
Perge, J. A. et al. Reliability of directional information in unsorted spikes and local field potentials recorded in human motor cortex. Journal of neural engineering 11, 046007 (2014).
Bacher, D. et al. Neural point-and-click communication by a person with incomplete locked-in syndrome. Neurorehabilitation and neural repair 29, 462-471 (2015).
Buzsaki, G., Anastassiou, C. A. & Koch, C. The origin of extracellular fields and currents—EEG, ECoG, LFP and spikes. Nat Rev Neurosci 13, 407-420, doi:10.1038/nrn3241 (2012).
Manning, J. R., Jacobs, J., Fried, I. & Kahana, M. J. Broadband shifts in local field potential power spectra are correlated with single-neuron spiking in humans. Journal of Neuroscience 29, 13613-13620 (2009).
Engelhard, B., Ozeri, N., Israel, Z., Bergman, H. & Vaadia, E. Inducing gamma oscillations and precise spike synchrony by operant conditioning via brain-machine interface. Neuron 77, 361-375 (2013).
Flint, R. D., Scheid, M. R., Wright, Z. A., Solla, S. A. & Slutzky, M. W. Long-Term Stability of Motor Cortical Activity: Implications for Brain Machine Interfaces and Optimal Feedback Control. J Neurosci 36, 3623-3632, doi:10.1523/ineurosci.2339-15.2016 (2016).
Slutzky, M. W. & Flint, R. D. Physiological properties of brain-machine interface input signals. J Neurophysiol 118, 1329-1343, doi:10.1152/jn.00070.2017 (2017).
Slutzky, M. W. Brain-machine interfaces: powerful tools for clinical treatment and neuroscientific investigations. The Neuroscientist, 1073858418775355 (2018).
Lee, J. H. et al. A contusive model of unilateral cervical spinal cord injury using the infinite horizon impactor. Journal of visualized experiments: JoVE (2012).
Alam, M. et al. Electrical neuromodulation of the cervical spinal cord facilitates forelimb skilled function recovery in spinal cord injured rats. Experimental neurology 291, 141-150 (2017).

(56) References Cited

OTHER PUBLICATIONS

Klimstra, M. & Zehr, E. P. A sigmoid function is the best fit for the ascending limb of the Hoffmann reflex recruitment curve. Experimental brain research 186, 93-105 (2008).
Ludwig, K. A. et al. Using a common average reference to improve cortical neuron recordings from microelectrode arrays. Journal of neurophysiology 101, 1679-1689 (2009).
Khorasani, A., Foodeh, R., Shalchyan, V. & Daliri, M. R. Brain Control of an External Device by Extracting the Highest Force-Related Contents of Local Field Potentials in Freely Moving Rats. IEEE Transactions on Neural Systems and Rehabilitation Engineering 26, 18-25 (2018).
Irvine, K.-A et al. The Irvine, Beatties, and Bresnahan (IBB) forelimb recovery scale: an assessment of reliability and validity. Frontiers in neurology 5, 116 (2014).
Koivuniemi, A. S. & Otto, K. J. Asymmetric versus symmetric pulses for cortical microstimulation. IEEE Transactions on Neural Systems and Rehabilitation Engineering 19, 468-476 (2011).
Slutzky, M. W., Jordan, L. R., Lindberg, E. W., Lindsay, K. E. & Miller, L. E. Decoding the rat forelimb movement direction from epidural and intracortical field potentials. Journal of neural engineering 8, 036013 (2011).
Dietz, V. & Fouad, K. Restoration of sensorimotor functions after spinal cord injury. Brain 137, 654-667 (2013).
Walsh, L. D., Moseley, G. L., Taylor, J. L. & Gandevia, S. C. Proprioceptive signals contribute to the sense of body ownership. The Journal of physiology 589, 3009-3021 (2011).
Thrasher, A., Graham, G. M. & Popovic, M. R. Reducing muscle fatigue due to functional electrical stimulation using random modulation of stimulation parameters. Artificial organs 29, 453-458 (2005).
Friedenberg, D. A. et al. Neuroprosthetic-enabled control of graded arm muscle contraction in a paralyzed human. Scientific reports 7, 8386 (2017).
Sharpe, A. N. & Jackson, A. Upper-limb muscle responses to epidural, subdural and intraspinal stimulation of the cervical spinal cord. Journal of neural engineering 11, 016005 (2014).
Angeli, C. A., Edgerton, V. R., Gerasimenko, Y. P. & Harkema, S. J. Altering spinal cord excitability enables voluntary movements after chronic complete paralysis in humans. Brain 137, 1394-1409, doi: 10.1093/brain/awu038 (2014).
Samejima, S. et al., "Brain-Computer-Spinal Interface Restores Upper Limb Function After Spinal Cord Injury," EMB IEEE Transactions on Neural Systems and Rehabilitation Engineering, Vo. 29, 2021, pp. 1233-1242.
Rejc, E., Angeli, C. A., Atkinson, D. & Harkema, S. J. Motor recovery after activity-based training with spinal cord epidural stimulation in a chronic motor complete paraplegic. Scientific reports 7, 13476 (2017).
Butt, M., Alataris, K., Walker, A. & Tiede, J. F702 histological findings using novel stimulation parameters in a caprine model. European Journal of Pain Supplements 5, 188-189 (2011).
Gerasimenko, Y. P. et al. Noninvasive Reactivation of Motor Descending Control after Paralysis. J Neurotrauma 32, 1968-1980, doi:10.1089/neu.2015.4008 (2015).
Utz, M. et al. In Vivo Measurements of the Frequency-Dependent Impedance of the Spinal Cord. bioRxiv, 252965 (2018).
Joseph, L. & Butera, R. J. High-frequency stimulation selectively blocks different types of fibers in frog sciatic nerve. IEEE Trans Neural Syst Rehabil Eng 19, 550-557, doi: 10.1109/tnsre.2011.2163082 (2011).
Al-Kaisy, A. et al. Sustained effectiveness of 10 kHz high-frequency spinal cord stimulation for patients with chronic, low back pain: 24-month results of a prospective multicenter study. Pain Medicine 15, 347-354 (2014).

Donati, A. R. et al. Long-term training with a brain-machine interface-based gait protocol induces partial neurological recovery in paraplegic patients. Scientific reports 6, 30383 (2016).
Wang, D. et al. Long-term decoding stability of local field potentials from silicon arrays in primate motor cortex during a 2D center out task. Journal of neural engineering 11, 036009 (2014).
Flint, R. D., Wright, Z. A., Scheid, M. R. & Slutzky, M. W. Long term, stable brain machine interface performance using local field potentials and multiunit spikes. J Neural Eng 10, 056005, doi:10.1088/1741-2560/10/5/056005 (2013).
Milekovic, T. et al. Stable long-term BCI-enabled communication in ALS and locked-in syndrome using LFP signals. Journal of neurophysiology (2018).
Milekovic, T. et al. Volitional control of single-electrode high gamma local field potentials (LFPs) by people with paralysis. Journal of neurophysiology (2019).
Nishimura, Y., Perlmutter, S. I., Eaton, R. W. & Fetz, E. E. Spike-timing-dependent plasticity in primate corticospinal connections induced during free behavior. Neuron 80, 1301-1309 (2013).
McPherson, J. G., Miller, R. R. & Perlmutter, S. I. Targeted, activity-dependent spinal stimulation produces long-lasting motor recovery in chronic cervical spinal cord injury. Proceedings of the National Academy of Sciences 112, 12193-12198 (2015).
Hollis II, E. R. et al. Ryk controls remapping of motor cortex during functional recovery after spinal cord injury. Nature neuroscience 19, 697 (2016).
Hilton, B. J. et al. Re-establishment of cortical motor output maps and spontaneous functional recovery via spared dorsolaterally projecting corticospinal neurons after dorsal column spinal cord injury in adult mice. Journal of Neuroscience 36, 4080-4092 (2016).
Zickler, C., Halder, S., Kleih, S. C., Herbert, C. & Kubler, A. Brain painting: usability testing according to the user-centered design in end users with severe motor paralysis. Artificial intelligence in medicine 59, 99-110 (2013).
Grahn, P. J. et al. Wireless control of intraspinal microstimulation in a rodent model of paralysis. Journal of neurosurgery 123, 232-242 (2015).
Xu, Q., Hu, D., Duan, B. & He, J. A fully implantable stimulator with wireless power and data transmission for experimental investigation of epidural spinal cord stimulation. IEEE Transactions on Neural Systems and Rehabilitation Engineering 23, 683-692 (2015).
Lo, Y.-K et al. A fully integrated wireless SoC for motor function recovery after spinal cord injury. IEEE transactions on Biomedical Circuits and Systems 11, 497-509 (2017).
Shahdoost, S. et al. A brain-spinal interface (BSI) system-on-chip (SoC) for closed-loop cortically-controlled intraspinal microstimulation. Analog Integrated Circuits and Signal Processing 95, 1-16 (2018).
Mavoori, J., Jackson, A., Diorio, C. & Fetz, E. An autonomous implantable computer for neural recording and stimulation in unrestrained primates. Journal of neuroscience methods 148, 71-77 (2005).
Wolpaw, J. R. et al. Independent home use of a brain-computer interface by people with amyotrophic lateral sclerosis. Neurology 91, e258-e267 (2018).
Ranganathan, V. et al. Neural closed-loop implantable platform: a modular FPGA-based neural interface for closed-loop operation. 2019 9th International IEEE/EMBS Conference on Neural Engineering (NER) (Accepted) (2019).
Popovic, M. R., Popovic, D. B. & Keller, T. Neuroprostheses for grasping. Neurological research 24, 443-452 (2002).
Minev, I. R. et al. Biomaterials. Electronic dura mater for long-term multimodal neural interfaces. Science 347, 159-163, doi:10.1126/science.1260318 (2015).

* cited by examiner

HIGH FREQUENCY EPIDURAL STIMULATION TO CONTROL SENSATION

CROSS-REFERENCE TO RELATED APPLICATIONS

This application is a National Stage of International Application No. PCT/2021/035390, filed Jun. 2, 2021, which claims the benefit of U.S. Provisional Application No. 63/033,644, filed Jun. 2, 2020, the disclosures of which are expressly incorporated herein by reference in their entirety.

STATEMENT OF GOVERNMENT LICENSE RIGHTS

This invention was made with government support under Grant No. EEC1028725, awarded by the National Science Foundation. The government has certain rights in the invention.

BACKGROUND

Spinal cord injury (SCI) results in lifelong functional impairments. The disrupted connection between brain and spinal cord leads to a significant decline in quality of life (QOL) and an increase in the cost of healthcare. Currently, approximately half a million people per year newly suffer from SCI around the globe. Almost half of the total population with SCI have incomplete tetraplegia. The highest priority for improving the personal QOL in people with tetraplegia is restoring hand and arm function. To approach this demand, the research community has presented enormous on-going endeavors for clinical interventions. However, there is currently no cure for paralyzed hands and arms following SCI.

Emerging technology relies on electrical stimulation of the spine to mimic the muscle-activating signals that the brain would ordinarily send to limbs through the spine. However, it is still difficult to properly modulate such signals such that the desired motor function is achieved, while the patient does not experience sensation of pain. Accordingly, systems and methods are needed for an effective delivery of electrical stimulus to the injured spine and further toward the limbs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a method for restoring physiological function in a subject having a neurological impairment includes generating a stimulation pattern. The stimulation pattern includes pulses at a first frequency, and the pulses of the stimulation pattern are modulated by a modulation pattern at a second frequency. The second frequency is higher than the first frequency. The method also includes stimulating a region of the spinal cord with the stimulation pattern via one or more electrodes.

In one aspect, the method also includes: detecting neural signals generated in a brain of the subject; and decoding the neural signals, where decoded neural signals are representative of intended movements of the subject. The pulses at the first frequency are based on the decoded neural signals.

In one aspect, the neural signals generated in the brain of the subject are detected as local field potential (LFPs).

In another aspect, the method also includes: rejecting stimulation artifacts from the neural signals using a sample-and-hold method; and applying a common average reference (CAR) filter to remove common voltage components in the neural signals.

In one aspect, the method also includes decoding subject's intention for physiological function in real-time as a decoded movement by applying canonical correlation analysis (CCA) weights.

In one aspect, the electrodes are epidural electrodes.

In another aspect, the stimulation pattern is at least in part produced by an implantable autonomous Field-Programmable Gate Array (FPGA) device.

In one aspect, the second frequency is within a range of 5 kHz and 20 KHz.

In one aspect, the first frequency is within a range of 5 Hz and 300 Hz.

In one aspect, the region of the spinal cord is stimulated through epidural, subdural, intradural, intraspinal, transvertebral, intra-muscular, spinal roots, spinal nerves, or peripheral nerves stimulation.

In one embodiment, a system for restoring motor function in a subject having a neurological impairment includes: a stimulating component proximate to the spinal cord of the subject. The stimulating component is configured to electrically stimulate the spinal cord based on a stimulation pattern. The stimulation pattern includes pulses at a first frequency that are modulated by a modulation pattern at a second frequency, where the second frequency is higher than the first frequency.

In one aspect, the stimulating component is implanted proximately to the spinal cord of the subject.

In another aspect, the stimulating component is worn externally proximate the spinal cord of the subject.

In one aspect, the stimulating component includes electrodes configured for transmitting the stimulation pattern to the spine.

In one aspect, the electrodes are epidural electrodes.

In one aspect, the system is further configured for: detecting neural signals generated in a brain of the subject; and decoding the neural signals, where decoded neural signals are representative of intended movements of the subject; and where the pulses at the first frequency are based on the decoded neural signals.

In one aspect, the neural signals generated in the brain of the subject are detected as local field potential (LFPs).

In one aspect, the stimulating component includes an implantable autonomous Field-Programmable Gate Array (FPGA) device.

In one aspect, the first frequency is within a range of 5 Hz and 300 Hz, and the second frequency is within a range of 10 kHz and 20 KHz.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been described, it will be appreciated that various changes can be made therein without departing from the spirit and scope of the invention.

The inventive technology is directed to utilizing cortical activity patterns to control electrical stimulation to the nervous system (e.g., spine) to enable function. In some embodiments, the inventive technology includes detecting neural signals, such as local field potentials, generated in the brain of the subject to predict/determine intended movements of the subject. For example, detected neural signals could indicate that the subject intends to move one of their upper limbs that is paralyzed or has a reduced motor function because of the spinal cord injury. In some embodiments, the neural signals are local field potential (LFPs), such as high-gamma LFP bands.

The method can further include generating a stimulation pattern based on the decoded neural signals and stimulating a region of the spinal cord below the injury with the stimulation pattern. When received by the spine, the stimulation pattern indicates intended movements of the subject (e.g., intended movement of a limb of the subject). In some embodiments, the spinal cord can be epidurally stimulated. The detection of neural signals related to motor intention of the subject and subsequent stimulation of the spinal cord of the subject may promote motor function restoration and rehabilitative effect. For example, the stimulation can help restore volitional control of the paralyzed limb.

Specific patterns of stimulation may enable movement while simultaneously reducing any unpleasant sensations arising from the stimulation. In some embodiments, the decoded neural signal may have a frequency within a range of 5 Hz to 300 Hz. In some instances, such stimulation at a relatively low frequency may cause pain or discomfort in test subjects when being applied to the spinal cord. Therefore, in some embodiments, the stimulation waveform is frequency modulated with a modulation frequency (also referred to as a carrier frequency) to produce a stimulation pattern that reduces pain or other unpleasant sensation in the subject, while retaining the desired effect of stimulating the damaged spine to produce a target motion of the limb. In some embodiments, such modulation or carrier frequency may be within a range of 5 kilohertz (KHz) to 20 kHz. In some embodiments, the stimulation pattern is produced by a fully implantable autonomous Field-Programmable Gate Array (FPGA) device given a relatively low computational complexity and expected high clinical viability for restoration of limb function after spinal cord injury. The inventive technology is described in the context of spine stimulation, however, in different embodiments the inventive technology may also be applicable to Parkinson's disease, multiple sclerosis stroke, dystonia, amyotrophic lateral sclerosis, cerebral palsy, or other neurological impairment.

Figure 1A:
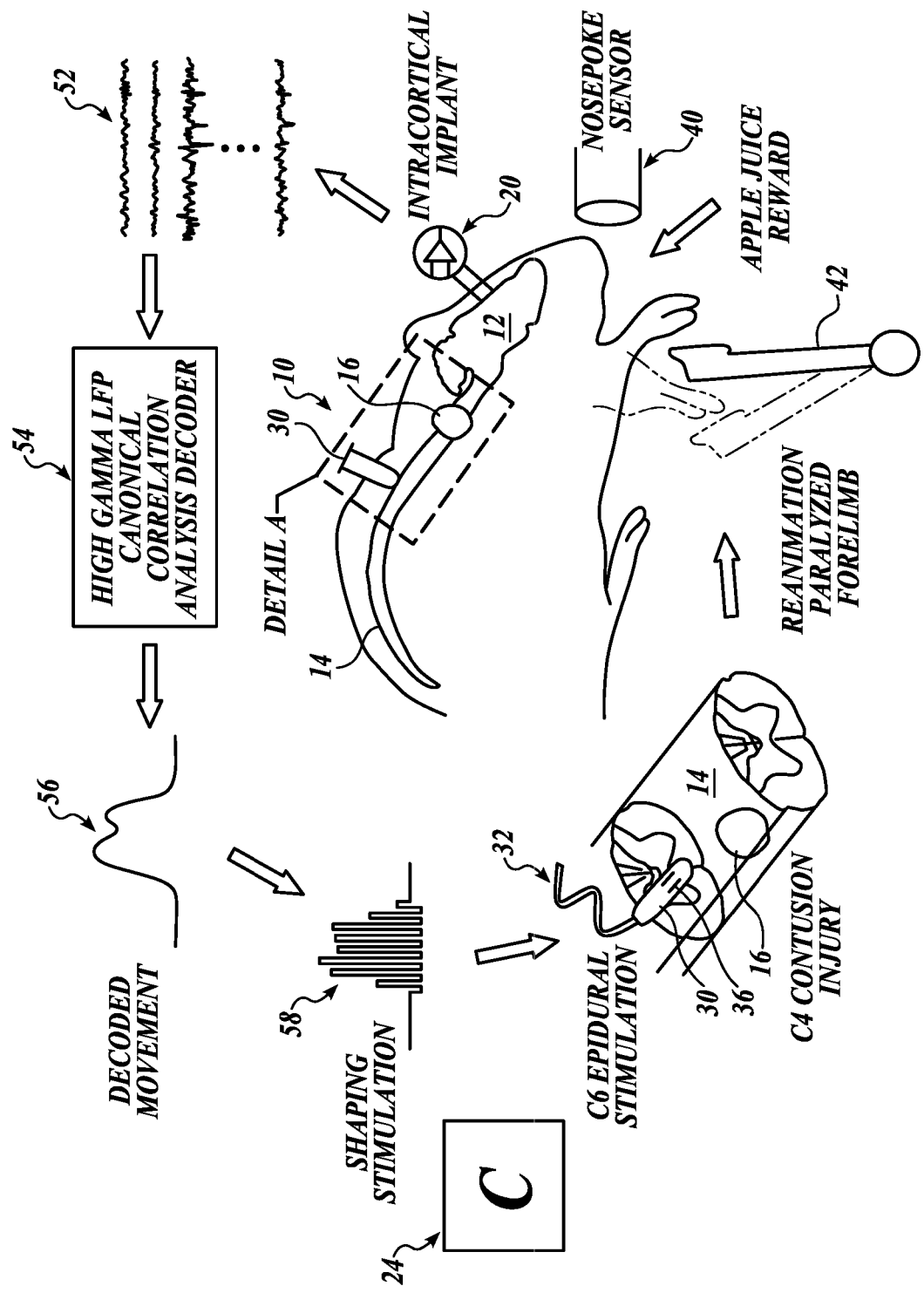
FIG. 1A is a schematic flowchart illustrating delivery of the spinal stimulation in accordance with an embodiment of the present technology.

FIG. 1A is a schematic flowchart illustrating delivery of the spinal stimulation in accordance with an embodiment of the present technology. In some embodiments, test animal 10 is equipped with an intracortical implant 20 that can register brain signals (also referred to as neural signals) 52 recorded from the animal's brain 12. To overcome the limitations associated with spike-based decoding, embodiments of the present technology may detect and/or record local field potentials (LFPs) which have multiple potential advantages over detecting just the spikes. LFPs are extracellular potentials, mostly postsynaptic, that are recorded via intracortical arrays. The illustrated LFP activity 52 correlates with movement-related spike activity in the 200-400 Hz (high-gamma) band and can provide unique movement-relevant information separate from spikes. Multiunit spikes and LFPs show similar decoding performance and stability over months. Therefore, advantages of LFPs include less frequent calibration by skilled persons. Furthermore, LFP decoders 54 also have lower bandwidth requirements than spike decoders, which translates into a lower computational power demand.

In operation, decoded waveforms 56 represent signals that can be interpreted by animal's spine 14 as follows. A spinal injury 16 prevents or at least impedes normal neural communication between the brain 12 and spine 14 of the test animal 10. To overcome or reduce the effects of the spinal injury 16, the decoded movement 56 may be implemented (epidurally or otherwise) via an implant 30 to transfer the decoded waveform (signal) 56 onto the spine of the animal. When stimulated by the decoded waveforms 56, the spine activates the limb of the trained animal 10 to perform a rewarded activity (e.g., a movement of the lever 42, positioning animal's body with respect to a nosepoke sensor 40, etc.). In some embodiments, shaping stimulation 58 may be used to modulate the decoded waveform 56. As further explained below, such shaping stimulation 58 may improve the control of movement by the test subject (animal or human). Also shown in 58 is an overlap frequency comprised of short pulses at 5-20 kHz that can reduce or eliminate pain sensation or irritation experience by the test subject due to the stimulation.

In different embodiments, data (e.g., decoded movement signal 56) may be transferred to the epidural implant 30 through an electrical cable 32 or wirelessly. In some embodiments, the decoded waveform 56 and the shaping stimulation 58 is generated by a controller 24 that includes a Field Programmable Gate Array (FPGA). In some embodiments, the controller with FPGA may be integral to the epidural implant 30.

The epidural implant 30 may stimulate the spine 14 through epidural electrodes 36. In the context of this application, the inventive technology is illustrated with respect to the epidural stimulation for brevity and simplicity. However, in different embodiments the inventive technology is implementable to epidural, subdural, intradural, intraspinal, transvertebral, intra-muscular, spinal roots, spinal nerves, peripheral nerves or other stimulation.

Figure 1B:
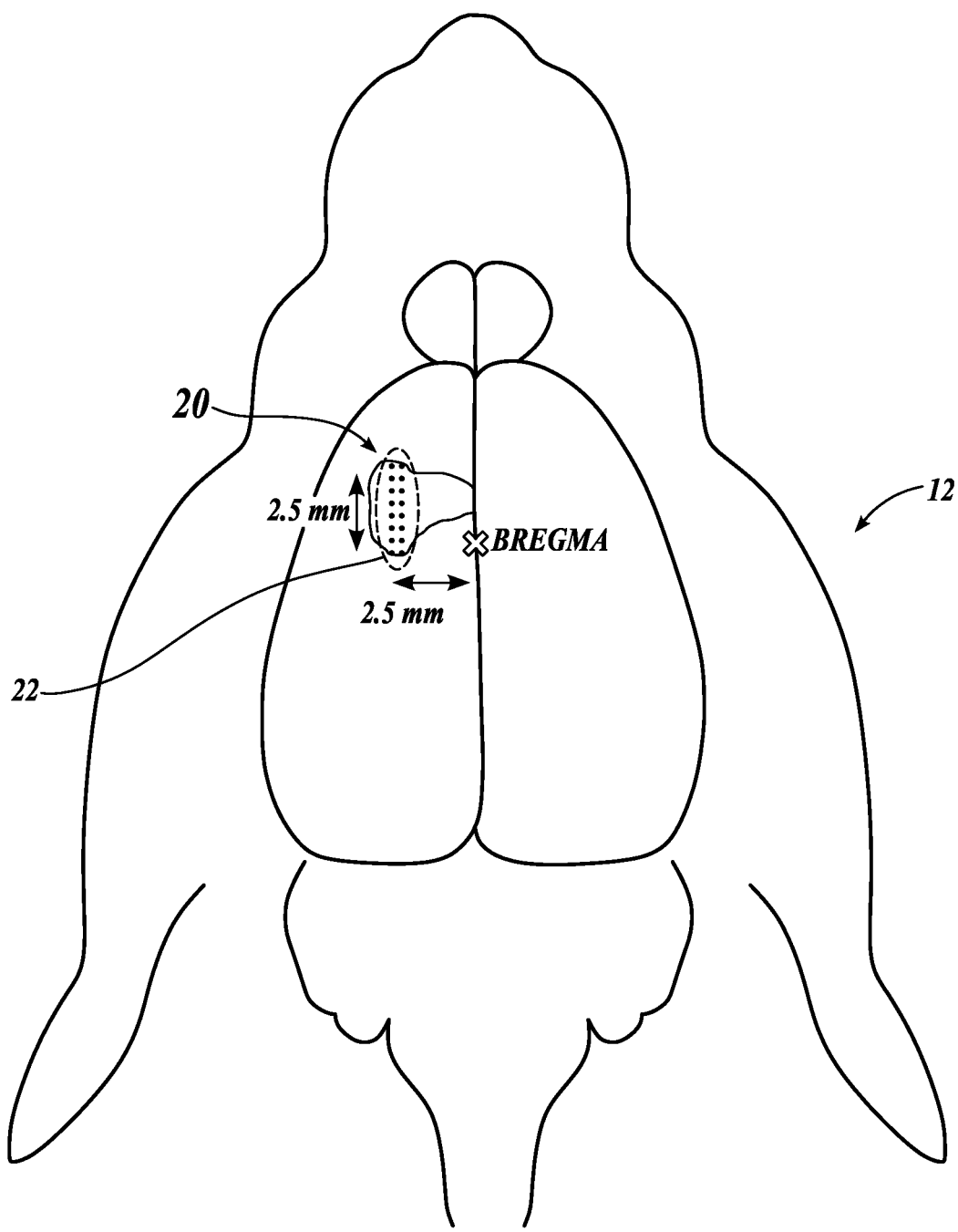
FIG. 1B illustrates placement of an intracortical implant for reading brain signals in accordance with an embodiment of the present technology.

FIG. 1B illustrates placement of an intracortical implant 20 for reading brain signals in accordance with an embodiment of the present technology. Illustrated intracortical implant 20 includes an 8×2 microarray that is about 2.5 mm long. The center of the forelimb area is located 1.5 mm rostral and 2.5 mm lateral to bregma. The arrays are inserted 1.5 mm below the brain surface to record the activity of pyramidal neurons in layer V.

For the experiment described with respect to FIG. 1A, the intracortical implant 20 is implanted in the left forelimb sensorimotor cortex. In other embodiments, the intracortical implant 20 may be implanted in different areas depending on the desired effect to be induced by the epidural (or other) implant 30 that ultimately receives processed signals that were first collected by the intracortical implant 20.

Figure 2:
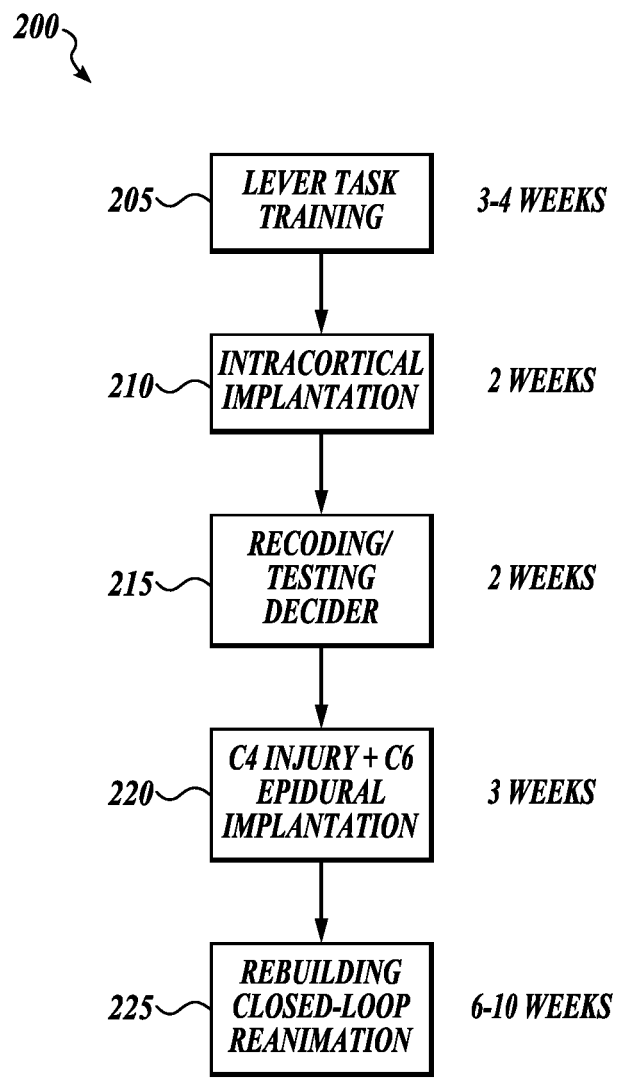
FIG. 2 is a flowchart of a method for delivering spinal stimulation in accordance with an embodiment of the present technology.

FIG. 2 is a flowchart of a method for delivering spinal stimulation in accordance with an embodiment of the present technology. The flowchart illustrates a protocol for a study performed in eleven female Long Evans rats (250-360 g). Block 205 corresponds to training of the test animals on a novel lever task for three to four weeks to reach competency defined as more than 60 lever pushes with the maximum range of extension within ten minutes. Once the animals met the criteria, they received implantation of intracortical electrodes for measuring multi-channel LFPs followed by a one-week recovery period in block 210. In block 215, brain recording and offline decoding of the lever movements are performed based on recorded multi-channel LFPs. In block 220, test animals receive a right lateralized C4 contusion injury and implantation of epidural electrodes at the right C6 spinal segment. After a two- to three-week recovery period, the animals are retrained for the lever task in the injured condition and recording data are refit with the LFP decoder. In block 225, the efficacy of LFP-controlled epidural stimulation is tested in animals with severe SCI.

In a controlled experiment, eleven animals underwent lever training and post-injury decoding. Five of these animals completed the brain-controlled reanimation. Some details of these controlled experiments are described below.

Lever Task Training

The lever push task was newly created for animals with severely impaired forelimb function to keep them engaged in the task while maintaining a head-mounted external recording and stimulation system. The behavior arena consisted of a translucent acrylic box with a slit in both sides of the platform. The joystick was in the right slit and measured the two-dimension lever displacement. A nose poke sensor and a fluid tube for reward were placed on the front wall (as illustrated in FIG. 1A above).

Animal's task included placing the nose in front of the nosepoke sensor 40 to position their bodies and to ensure engagement with the task. Simultaneously, the rat had to reach and push the lever 42 backward to the predetermined reward threshold. The lever push requires shoulder and elbow extension to complete. After successful lever press trials, the animals were given an apple juice reward. The training was performed ten to twenty minutes each day, five days per week for three to four weeks to achieve proficiency before surgery. The rats were water restricted between sessions. After each session, they were given one-hour water access per day and free water over weekends. The lever trajectories and the nose poke sensor signals were recorded as the functional measures reflecting synergistic shoulder and elbow extension movement as well as body position.

Cortical Surgery

All surgeries were performed using sterile techniques while the animal was under general anesthesia using 2-3% isoflurane in O2. Body temperature was maintained at 37° C. using a heating pad during surgeries and until fully recovered. Baytril 0.05 mg/kg was preoperatively administered. After a craniotomy and removal of the dura matter, sterilized 16-wire tungsten microelectrode arrays (40 μm diameter) were inserted into rostral and caudal forelimb areas of the sensorimotor cortex 1.5 mm below the brain surface to record pyramidal neuron activity in layer V (as illustrated in FIG. 1B). Postoperative Buprenorphine 0.5 mg/kg was administered twice per day for three days.

Spinal Surgery

After the C4 unilateral laminectomy, the right lateralized C4 contusion injury was performed using a force control closed-loop system, the Infinity Horizon Impactor (Precision Systems and Instrumentation, LLC., Fairfax Station, VA). The impact force was set at 200 kdyn. The severity of injury was consistent across animals. Two bundled electrode wires (11 μm diameter, AS631, Cooner wire) were stabilized on a polyimide sheet (5 mm×1.5 mm×46 μm) by epoxy. One mm of Teflon insulation was removed from the two wires. After the C7 unilateral laminectomy, the sterilized epidural implant was placed between the C5-C6 lamina and the dura matter from the caudal side of C6. Subsequently, the caudal side of the epidural implant was sutured on the dura over the dorsal aspect of the right C6 level (FIG. 1A). A loop of wires covered by a catheter was formed near their site of insertion to provide stress relief. A common ground wire was inserted subcutaneously near the shoulder on the right forelimb. The connector was placed on the headcap shared with the cortical implant.

Motor Evoked Potential Recording with Nerve Cuff and Epidural Stimulation

Motor evoked potential (MEP) tests were performed in acute terminal surgery settings under urethane anesthesia to test recruitment curves of triceps activation by radial nerve stimulation and epidural stimulation. The epidural stimulator was implanted on the dura at the right C6 spinal segment as described above. The ground wire was implanted in the shoulder muscle. Bipolar electrodes were then inserted in the right triceps for electromyographic (EMG) recording (AS631, Cooner wire). After the right radial nerve was exposed around the outlet from the brachial plexus, the nerve cuff (Micro Cuff Sling, CorTec, Germany) was placed around the nerve for bipolar stimulation. Monophasic (single, 500 μs, monophasic, cathodic) and biphasic (single, 500 μs, biphasic, cathodic-first, charge balanced) stimulation pulses, 30 pulses each parameter at 2 Hz, were delivered. The experiments were performed with three stimulation conditions including regular epidural stimulation, epidural stimulation with a 10k Hz carrier frequency, and nerve cuff stimulation (NCS) with various current intensities using an analog stimulus isolator (Model 2100 Isolated Pulse Stimulator. AM System, Sequim, WA). Each of the three conditions had N=6 consisting of 3 animals×2 stimulation parameters (monophasic and biphasic pulses).

The signals were amplified (1000×) using the Tucker Davis Technologies (TDT) system (Alachua, FL). MEPs were analyzed offline using custom MATLAB scripts. Triceps EMG signals were filtered (4th order Butterworth band-pass: 30-1000 Hz), and a single trial of MEP was defined as evoked responses during the 30 ms time window after each stimulation event. MEPs were subsequently processed to compute maximum peak to peak amplitude in the time window and calculate recruitment curves in triceps muscles.

The activation slopes of recruitment curves were computed as follows. The raw value of each peak to peak amplitude value was normalized by the maximum mean amplitude (from a set of 30 pulses) produced during the entire recording within each animal. A Boltzmann sigmoid function was fitted to the normalized recruitment curve to compute the slope for NCS, epidural stimulation with and without 10 KHz carrier frequency (also referred to as modulation frequency).

Brain Data Acquisition and Signal Processing

The decoding performance was examined in the pre-SCI and post-SCI conditions. LFP decoding stability across conditions was analyzed in seven animals. Brain-controlled epidural stimulation system was tested in five animals following SCI (one animal was involved in the both decoding stability and BCSI system tests).

The pre-amplified data was recorded using the TDT multichannel data acquisition system, at a 24.4 kHz sampling rate. Concomitantly, the continuous lever and nose poke signals were recorded in the same system. At least 50 pushes were recorded each recording session. The decoding procedure was used in both offline analysis by custom MATLAB code and online analysis in the TDT system.

Figure 3:
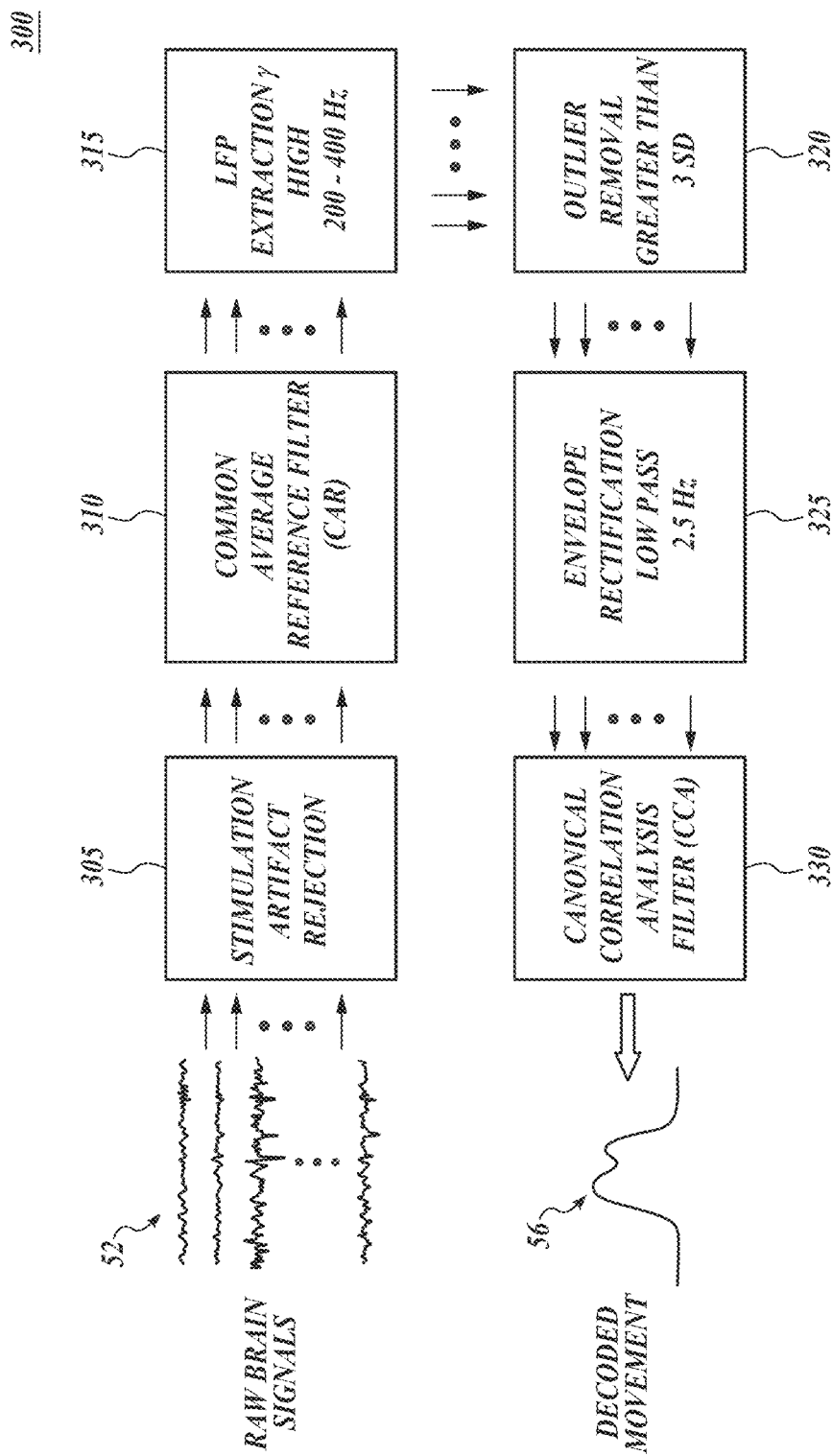
FIG. 3 is a flowchart of generating signal for spinal stimulation in accordance with an embodiment of the present technology.

FIG. 3 is a flowchart of generating signal for spinal stimulation in accordance with an embodiment of the present technology. In block 305, stimulation artifacts are removed from the raw brain signals 52 using the sample-and-hold method. When epidural stimulation is delivered, a sample-and-hold method is used for 2 ms after the stimulation event to remove the stimulation-induced artifact. Also, the intracortical signals might contain significant noises due to high impedance or connector problems. Therefore, in some embodiments, the following measurements are removed/filtered: (1) channels containing irregularly high amplitude signals, (ii) power spectrums not obeying 1/f frequency filtering, and (iii) movement related artifacts visible in spectrograms as high amplitude transient broadband events.

In block 310, a common average reference filter is applied to increase signal-to-noise (SNR) ratio of the recorded brain signals. After rejecting the stimulation-induced artifact, a common average reference (CAR) filter may be applied to increase the signal-to-noise ratio of the recorded signal. The CAR filter removes common voltage components mainly produced by the noise content across all channels. Next, the 16-channel brain data is filtered using, e.g., 4th order Butterworth, band-pass filter, forward, to the frequency band of interest. The 200-400 Hz band and 0-100 ms lag time may be selected since these parameters demonstrated, in an offline analysis, a relatively high correlation with the lever movement among the alternative frequency sub-bands and lag times. An outlier removal algorithm was applied to cap particularly high voltages at three times the standard deviation of each LFP signal.

In block 315, local field potential (LFP) features are extracted by applying a band-pass filter and artifacts with significant voltage amplitude were rejected to increase decoding performance. In some embodiments, based on the results of offline analysis 200-400 Hz envelopes of multi-channel LFPs are selected as features with 0-100 ms lag time to refine the decoding performance.

In some embodiments, after removing outliers greater than three standard deviation (SD) in block 320, the obtained envelopes are low-pass filtered in block 325, and multiplied by pre-created canonical correlation analysis (CCA) weights in block 330 to decode animal intention for forelimb movement in real-time as a decoded movement 56. The filtered signals are rectified and low-pass filtered (e.g., using a 4th order Butterworth filter, 2.5 Hz) to obtain multi-channel envelopes.

To obtain the highest movement related spectral components, a canonical correlation coefficient (CCA) filter may be applied on the multi-channel envelopes during the lever task. The CCA decoder presents relatively low computational complexity for high decoding performance compared to some other methods including principal component analysis and correlation coefficient-based feature reduction.

Post-Injury Decoding

After the recovery period following the contusion injury, the animals presented severe right forelimb paralysis showing minimum lever push movement (IBB scale: 1.6±0.93 (mean±SEM). N=5, 40-60 days post-injury). To obtain CCA weights after injury in the offline analysis, decoded movement is recreated based on the residual ability of extension movement in the paralyzed forelimb. The residual movement is used to detect the timing for insertion of artificial bell-shaped or square-shaped lever signals. This strategy for severe upper limb paralysis served as a proxy for imagined movements applied to human subjects with severe SCI.

Online Stimulation Protocol

The obtained CCA weights for each channel may be applied in the online closed-loop decoding algorithm on a benchtop computer. The decoded movement signal may be z-score normalized to have zero mean and unit standard deviation. This normalized signal is mapped between the motor threshold and maximum stimulation amplitude to control epidural (or other) stimulation. Whenever the decoded signal crosses a predetermined threshold while the nosepoke sensor was activated, the epidural stimulation is triggered.

As a non-limiting example, the epidural stimulation may include either monopolar biphasic square-wave pulses with 400 µs cathodic-first current or charge balanced monophasic square-wave pulses (pseudo-monophasic pulses) with 400 µs cathodic-first and 4 ms anodic at 1/10th current amplitude.

Pulses may be delivered in 15-40 pulse trains (also referred to as decoded movement 56) at 50-100 Hz. In different embodiments, frequency of the decoded movement 56 may be within ranges of 5-300 Hz, 10-200 Hz, 50-150 Hz, or within other ranges. The specific parameters can be determined based on the movement response in each animal, while the stimulation current amplitude can be scaled to evoke movement in each experiment (e.g., 300 µA to 1 mA).

In an illustrative experiment, two of five animals presented aversive behaviors to epidural stimulation including vocalization and forelimb withdraw. A 10 kHz carrier frequency (also referred as modulation frequency or overlap frequency) was applied with the monophasic stimulation consisting of 50 µs cathodic pulses with 50 µs intervals in a 400 µs train to reduce aversive behavior in test animals. In other embodiments, the carrier frequency may be within ranges of 5-20 kHz, 7-15 kHz. 10-20 kHz, or within other ranges.

The modulation of the current amplitude can also be exploited with the change of the decoded movement. For example, the decoded signal can be scaled from a predetermined threshold to the maximum decoded movement amplitude into the range 0 to 1.

Functional Assessment

During brain controlled epidural stimulation trials, trials with stimulation off trials may be randomly applied at 20-30% probability. To quantify functional changes, peak lever movements of each intended push can be compared between the brain-controlled stimulation condition and the stimulation off condition.

Statistical Procedures

In some embodiments, all data are reported as mean±SEM. Statistical evaluations may be performed by two-way ANOVA for parametric data. For other data, significance can be assessed using the non-parametric Wilcoxon signed-rank test. The analyses can be performed with software (e.g., SPSS, Chicago, IL, USA). In some embodiments, differences are considered significant at P<0.05.

Figure 4:
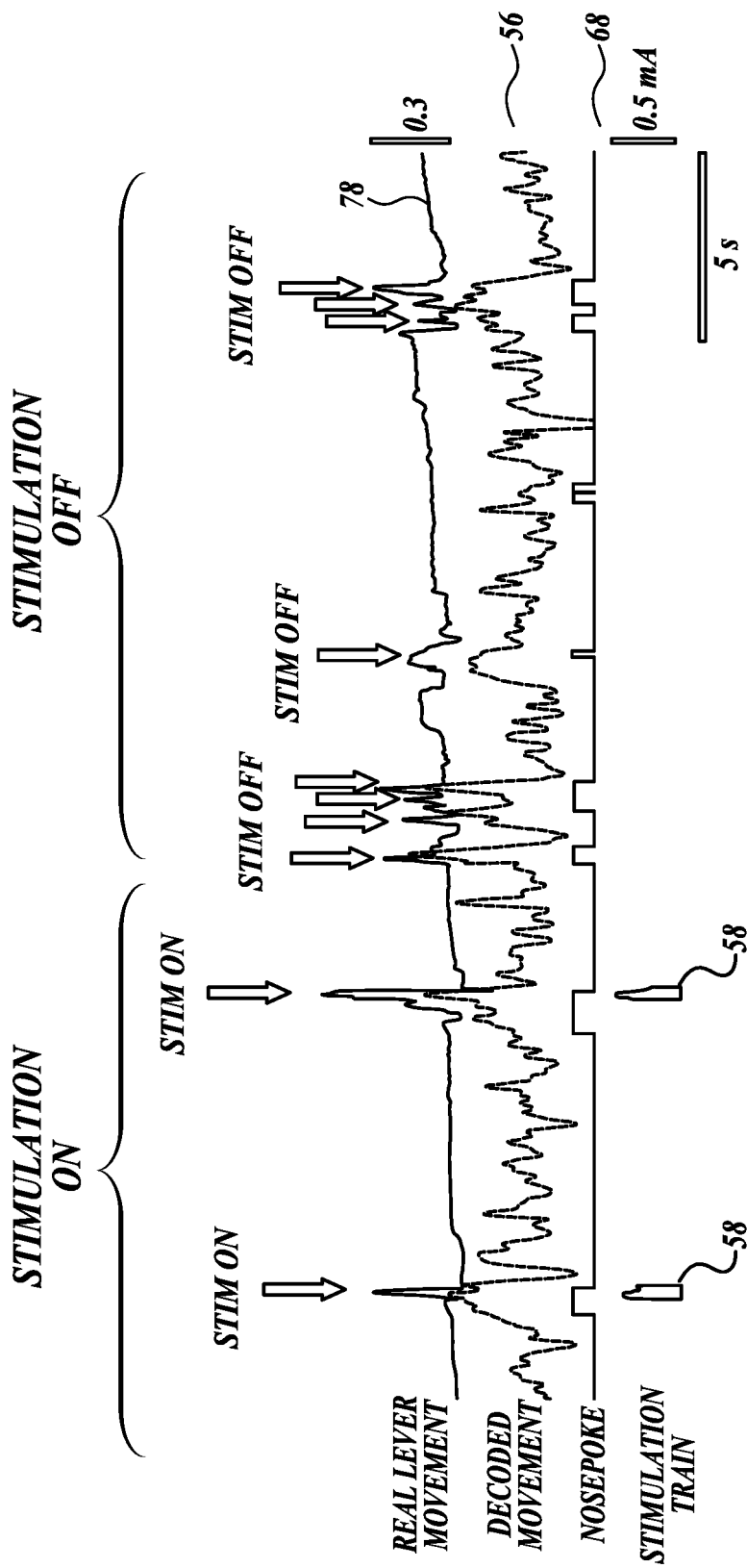
FIG. 4 is a graph illustrating spinal stimulation in accordance with embodiments of the present technology.

FIG. 4 is a graph illustrating spinal stimulation in accordance with embodiments of the present technology. The horizontal axis represents a timeline in seconds. The vertical axis represents simulation train in milliamperes (mA) (for the lines captioned as "simulation train," "nosepoke." and "decoded movement") and physical movement of the lever (for the line captioned "real lever movement"). First part of the horizontal axis ("stimulation ON") corresponds to the epidural implant 30 being active and capable of transmitting the decoded waveform 56 onto the spine of the test animal as the shaping stimulation 58. Second part of the horizontal axis ("stimulation OFF") corresponds to the epidural implant 30 being turned off and incapable of transmitting the decoded waveform 56 onto the spine of the test animal as the shaping stimulation 58, even though the decoded waveform 56 has been properly generated based on the brain signal 52.

During the first part of the test ("stimulation ON"), the test animal typically places its nose into the nosepoke 68 in preparation for the lever movement. Such placement of the test animal is registered by a pulse on the "nosepoke" curve. At around same time, brain of the test animal emits brain signals 52 signifying an attempt to move the front limb and actuate the lever. Brain signals 52 are decoded and processed as decoded waveform 56 using, for example, process described in conjunction with FIG. 3 above. When the decoded waveform 56 is transferred to the spine of the test animal as the shaping stimulation 58, lever is moved and its motion is recorded as real lever movement 78.

During the second part of the test ("stimulation OFF"), the test animal again places its nose into the nosepoke 68 in preparation for the lever movement, which registered by the pulse on the "nosepoke" curve. The brain of the test animal again emits brain signals 52 that are decoded and processed as decoded waveform 56. However, since the epidural implant is not active, the shaping stimulation 58 cannot be transferred to animal's spine, and the lever does not move to its full extent. Therefore, the curve titled "real lever movement" does not indicate maximum lever-activation peaks in this region.

Figure 5:
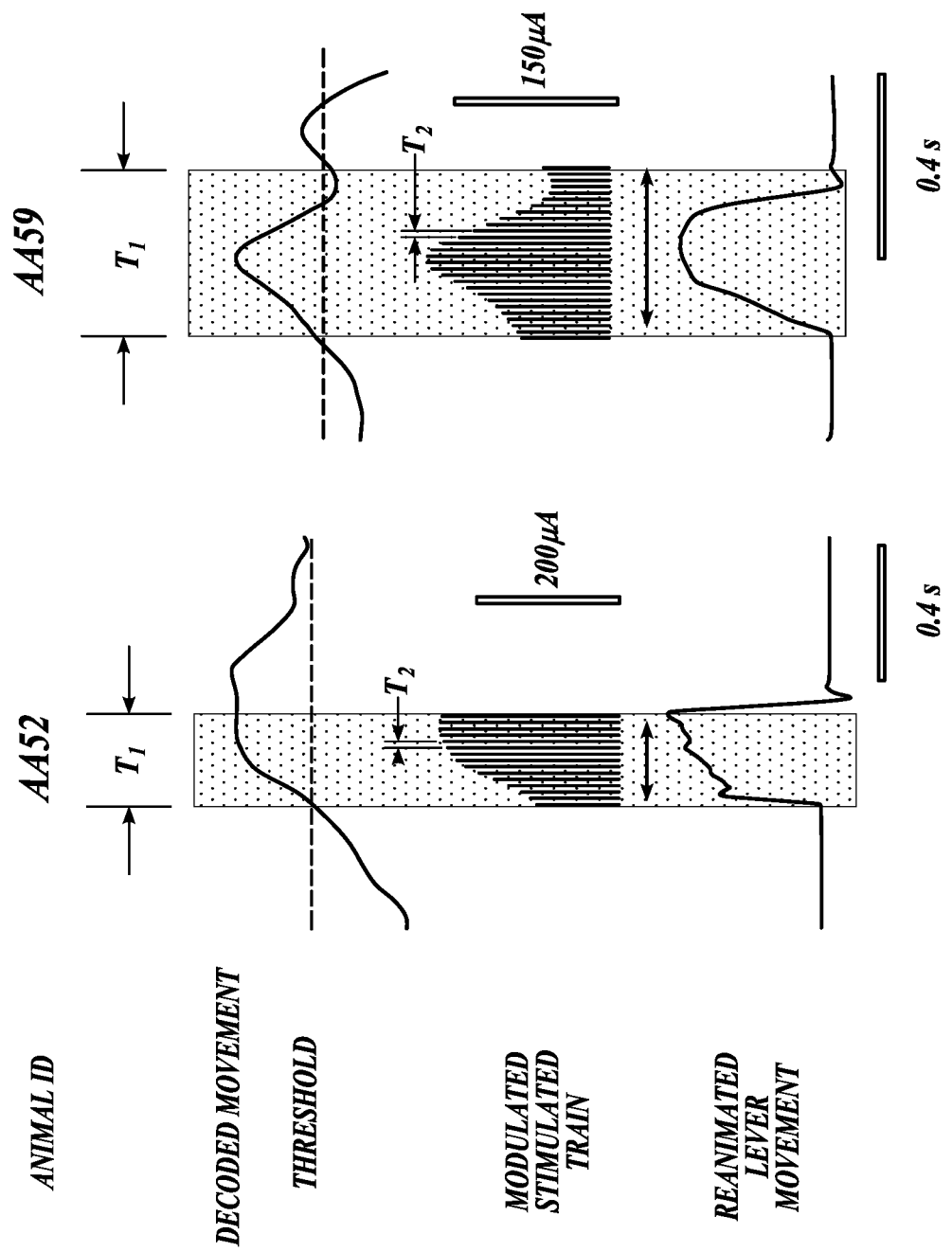
FIG. 5 is a graph illustrating spinal stimulation in accordance with an embodiment of the present technology.

FIG. 5 is a graph illustrating spinal stimulation in accordance with an embodiment of the present technology. Sample results are shown in two columns for test animals AA52 and AA59. In particular, FIG. 5 illustrates modulation of the decoded movement (decoded waveform) 56 at lower frequency (e.g., 5-300 Hz) in the upper row of graphs by the shaping stimulation 58 at a higher frequency (e.g. 5-20 KHz). When modulated using the modulation frequency, the decoded waveform 56 forms shaping stimulation 58 in the middle row of the graphs. As explained above, when the shaping stimulation 58 is epidurally or otherwise applied to the spine (or other neural tissue) of the animal, reanimated lever movement is generated as shown in the lower row of the graphs.

The decoded movement is characterized by time period T1, which in different embodiments may correspond to a frequency of 30 Hz or to frequencies within ranges of 50-100 Hz, 5-300 Hz, 10-200 Hz, 50-150 Hz, or other ranges. The shaping stimulation 58 is characterized by the carrier frequency having a time period T2, which in different embodiments may correspond to modulating frequency of 10 KHz or modulating frequencies within ranges of 5-20 KHz, 7-15 kHz. 10-20 KHz, or within other ranges. Collectively, these higher frequencies may be referred to as shaping frequencies or modulating frequencies. As explained above, some test animals demonstrate unpleasant aversive behaviors including vocalization and forelimb withdraw when subjected to the decoded waveform 56 alone. However, when the decoded waveform 56 is combined with the modulation frequency to produce the stimulation train 58, these adverse effects are in many cases eliminated or at least reduced.

Figure 6A:
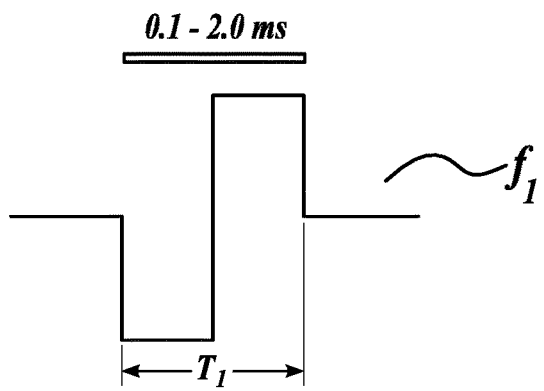
FIGS. 6A-6E are graphs illustrating pulse trains for spinal stimulation in accordance with embodiments of the present technology.
Figure 6B:
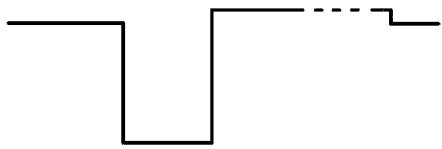

FIGS. 6A-6E are the graphs illustrating pulse trains for spinal stimulation in accordance with embodiments of the present technology. Such pulse trains may be suitable for different spinal or other neural stimulations. FIG. 6A shows a balanced biphasic pulse at the frequency of decoded waveform, for example, at frequency f1=30 Hz. FIG. 6B shows decoded waveform as a charge-balanced monophasic pulse followed by a long low counter charge.

Figure 6C:
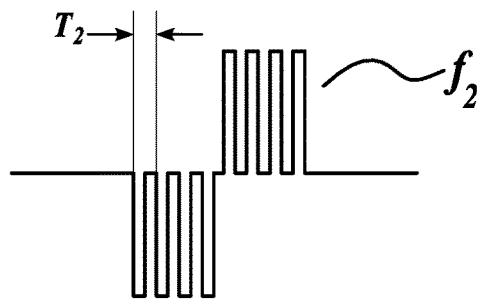
Figure 6D:
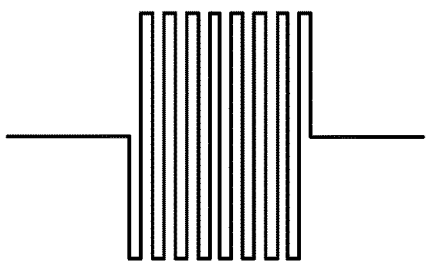
Figure 6E:
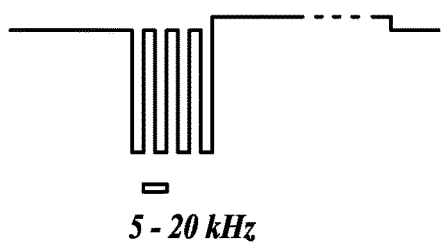

FIGS. 6C-6E show decoded simulation at a lower frequency f1 that is modulated with the modulating frequency f2. As explained above, such modulation may reduce pain that in some cases accompanies the spine stimulation. In some embodiments, frequency f2 may be 10 KHz. Therefore, FIGS. 6C-6E illustrate a modulated stimulation train 58 having the base frequency f1 of the decoded waveform and the modulating frequency f2. In particular, FIG. 6C illustrates charge-balanced dual pulse shaping stimulation; FIG. 6D illustrates a biphasic pulse; and FIG. 6E illustrates charge-balanced monophasic pulse followed by a long low counter charge.

Figure 7:
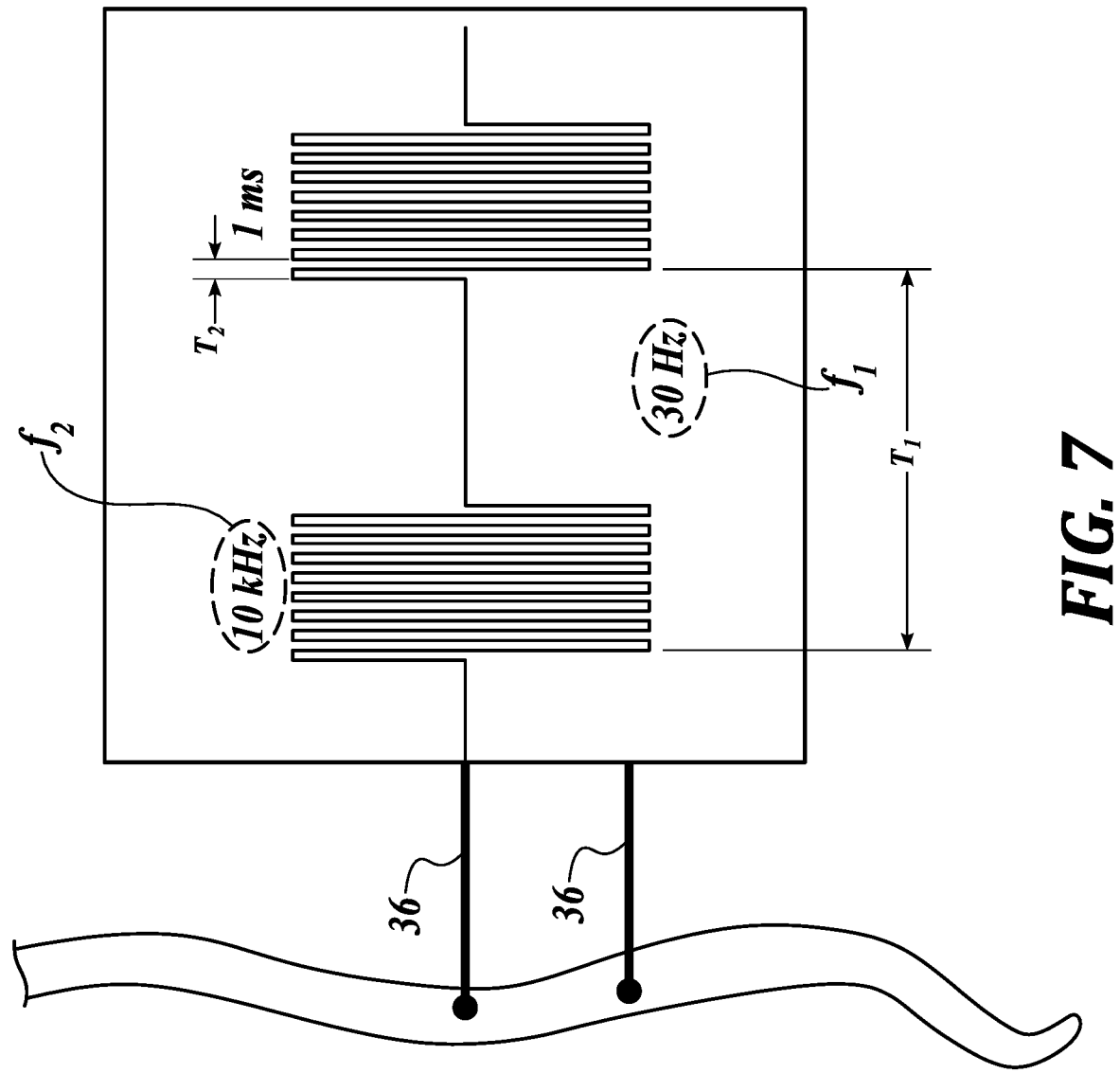
FIG. 7 is a graph illustrating delivery of pulse trains for spinal stimulation in accordance with embodiments of the present technology.

FIG. 7 is a graph illustrating delivery of pulse trains for spinal stimulation in accordance with embodiments of the present technology. The graph illustrates 1 ms pulses that are delivered at, for example, 30 Hz to the spine through epidural electrodes 36 of the epidural implant. These pulses are then modulated by the modulation frequency (carrier frequency) at, for example, 10 KHz.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Such computers, controllers and data processors may include a non-transitory computer-readable medium with executable instructions. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein. In the context of this disclosure, the term "about" means+/−5% of the stated value.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

What is claimed is:

1. A method for treating a neurological impairment in a subject by controlling sensation associated with a volitional motor task by the subject, the method comprising:
    detecting neural signals representative of an intended volitional movement of the subject;
    generating a stimulation pattern based on decoded neural signals;
    modulating an amplitude of the stimulation pattern in correspondence with the decoded neural signals;
    stimulating a region of a spinal cord of the subject with an electrical stimulation pattern, wherein the region is below an injury of the spinal cord, wherein the stimulation pattern comprises pulses that are based on the decoded neural signals, wherein the pulses of the stimulation pattern are delivered at a first frequency, wherein the pulses of the stimulation pattern are modulated by a modulation pattern at a second frequency that is configured for reducing pain sensation in the subject by modulating the first frequency, and wherein the second frequency is higher than the first frequency; and
    wherein the stimulation pattern is delivered via one or more electrodes configured for transmitting the stimulation pattern to the spinal cord,
    wherein, when received by the spinal cord, the stimulation pattern indicates intended volitional movements of the subject.

2. The method of claim 1, wherein the neural signals generated in the brain of the subject are detected as local field potential (LFPs).

3. The method of claim 2, further comprising:
    rejecting stimulation artifacts from the neural signals using a sample-and-hold method; and
    applying a common average reference (CAR) filter to remove common voltage components in the neural signals.

4. The method of claim 1, further comprising:
    decoding subject's intention for physiological function in real-time as a decoded movement by applying canonical correlation analysis (CCA) weights.

5. The method of claim 1, wherein the electrodes are epidural electrodes.

6. The method of claim 1, wherein the stimulation pattern is at least in part produced by an implantable autonomous Field-Programmable Gate Array (FPGA) device.

7. The method of claim 1, wherein the second frequency is within a range of 5 kHz and 20 kHz.

8. The method of claim 1, wherein the first frequency is within a range of 5 Hz and 300 Hz.

9. The method of claim 1, wherein the region of the spinal cord is stimulated through epidural, subdural, intradural, intraspinal, trans-vertebral, spinal roots, or spinal nerves.

10. A system for treating a neurological impairment in a subject by controlling sensation associated with a volitional motor task by the subject, the system comprising:
    a brain signal detection component configured for detecting neural signals representative of an intended volitional movement of the subject;
    a decoding component configured for generating a stimulation pattern based on decoded neural signals;
    a stimulating component configured to be disposed proximate to a spinal cord and below an injury of the subject, wherein the stimulating component is configured for electrically stimulating the spinal cord based on the stimulation pattern, wherein the stimulation pattern comprises pulses that are based on the decoded neural signals, wherein the pulses of the stimulation pattern are delivered at a first frequency that are modulated by a modulation pattern at a second frequency that is configured for reducing pain sensation in the subject by modulating the first frequency, and wherein the second frequency is higher than the first frequency,
    wherein, when received by the spinal cord, the stimulation pattern indicates intended volitional movements of the subject.

11. The system of claim 10, wherein the spinal cord is stimulated through epidural, subdural, intradural, intraspinal, trans-vertebral, spinal roots, or spinal nerves.

12. The system of claim 10, wherein the stimulating component is implantable proximately to the spinal cord of the subject.

13. The system of claim 10, wherein the stimulating component is wearable externally proximate the spinal cord of the subject.

14. The system of claim 10, wherein the stimulating component includes electrodes configured for transmitting the stimulation pattern to the spine.

15. The system of claim 14, wherein the electrodes are epidural electrodes.

16. The system of claim 10, wherein the neural signals generated in the brain of the subject are detected as local field potential (LFPs).

17. The system of claim 10, wherein the stimulating component comprises an implantable autonomous Field-Programmable Gate Array (FPGA) device.

18. The system of claim 10, wherein the first frequency is within a range of 5 Hz and 300 Hz, and wherein the second frequency is within a range of 10 kHz and 20 KHz.

* * * * *

UNITED STATES PATENT AND TRADEMARK OFFICE
CERTIFICATE OF CORRECTION

Page 1 of 1

PATENT NO. : 12,390,643 B2
APPLICATION NO. : 18/007948
DATED : August 19, 2025
INVENTOR(S) : Chet T. Mortiz et al.

It is certified that error appears in the above-identified patent and that said Letters Patent is hereby corrected as shown below:

On the Title Page

| Column | Line | |
|---|---|---|
| 1 | 2 | item (73), under Assignee, delete "(US)" and insert -- (US); Abed Khorasani, Seattle, WA (US) -- |

In the Claims

| Column | Line | |
|---|---|---|
| 12 | 53 | Claim 18, delete "KHz." and insert -- kHz. -- |

Signed and Sealed this
Eighteenth Day of November, 2025

John A. Squires
*Director of the United States Patent and Trademark Office*